United States Patent
Song

(10) Patent No.: US 10,632,223 B2
(45) Date of Patent: *Apr. 28, 2020

(54) MATERIALS THAT SHRINK IN ONE DIMENSION AND EXPAND IN ANOTHER DIMENSION

(71) Applicant: Kimberly-Clark Worldwide, Inc., Neenah, WI (US)

(72) Inventor: Xuedong Song, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 44 days.

This patent is subject to a terminal disclaimer.

(21) Appl. No.: 15/561,595

(22) PCT Filed: Sep. 29, 2015

(86) PCT No.: PCT/US2015/052789
§ 371 (c)(1),
(2) Date: Sep. 26, 2017

(87) PCT Pub. No.: WO2017/058152
PCT Pub. Date: Apr. 6, 2017

(65) Prior Publication Data
US 2018/0064842 A1 Mar. 8, 2018

(51) Int. Cl.
| | | |
|---|---|---|
| A61F 13/53 | (2006.01) |
| A61L 15/22 | (2006.01) |
| A61L 27/52 | (2006.01) |
| C08J 5/18 | (2006.01) |
| C08J 3/24 | (2006.01) |
| C08J 3/075 | (2006.01) |
| B29C 61/10 | (2006.01) |
| A61L 27/20 | (2006.01) |
| A61L 27/16 | (2006.01) |
| A61L 15/28 | (2006.01) |
| A61L 15/24 | (2006.01) |
| B29C 61/06 | (2006.01) |
| B29C 61/00 | (2006.01) |

(52) U.S. Cl.
CPC .............. *A61L 15/22* (2013.01); *A61F 13/53* (2013.01); *A61L 15/24* (2013.01); *A61L 15/28* (2013.01); *A61L 27/16* (2013.01); *A61L 27/20* (2013.01); *A61L 27/52* (2013.01); *B29C 61/003* (2013.01); *C08J 3/075* (2013.01); *C08J 3/243* (2013.01); *C08J 5/18* (2013.01); *A61F 2013/530437* (2013.01); *B29C 61/0608* (2013.01); *C08J 2333/26* (2013.01); *C08J 2405/04* (2013.01)

(58) Field of Classification Search
CPC .. C08L 33/26; C08L 5/04; A61L 15/24; A61L 15/28; A61L 27/16; A61L 27/20; A61L 15/22; A61L 27/52; A61F 13/53; A61F 2013/530437
See application file for complete search history.

(56) References Cited

U.S. PATENT DOCUMENTS

| | | | |
|---|---|---|---|
| 4,357,938 | A | 11/1982 | Ito et al. |
| 4,447,240 | A | 5/1984 | Ito et al. |
| 4,942,089 | A | 7/1990 | Genba et al. |
| 6,030,634 | A | 2/2000 | Wu et al. |
| 6,271,278 | B1 | 8/2001 | Park et al. |
| 6,605,349 | B2 | 8/2003 | Phillips |
| 6,960,617 | B2 | 11/2005 | Omidian et al. |
| 8,563,027 | B2 | 10/2013 | Jarrett et al. |
| 8,828,434 | B2 | 9/2014 | Su et al. |
| 8,916,683 | B2 | 12/2014 | Olsen et al. |
| 2010/0174021 | A1 | 7/2010 | Huie, Jr. et al. |
| 2010/0210752 | A1 | 8/2010 | Muratoglu et al. |
| 2012/0232502 | A1* | 9/2012 | Lowing ............... A61F 13/00 604/313 |
| 2014/0296425 | A1 | 10/2014 | Tew et al. |

(Continued)

FOREIGN PATENT DOCUMENTS

| | | |
|---|---|---|
| CN | 101608006 B | 4/2011 |
| CN | 101891946 B | 7/2012 |
| CN | 102226007 B | 9/2012 |

(Continued)

OTHER PUBLICATIONS

Omidian, H. et al., "Elastic, Superporous Hydrogel Hybrids of Polyacrylamide and Sodium Alginate," Macromolecular Bioscience, vol. 6, No. 9, 2006, pp. 703-710.
Sun, Jeong-Yun et al., "Highly Stretchable and Tough Hydrogels," Nature, Macmillan Publishers, vol. 489, Sep. 6, 2012, pp. 133-136.
Machine translation of JP 2005-526879 A to Munro et al., dated Sep. 8, 2005, 45 pages.
Wang, Jilong et al., 'Ion-linked double-network hydrogel with high toughness and stiffness,' Journal of Materials Science (2015)50:5458-5465.May 19, 2015.

(Continued)

*Primary Examiner* — Arti Singh-Pandey
(74) *Attorney, Agent, or Firm* — Kimberly-Clark Worldwide, Inc.

(57) ABSTRACT

A substrate includes a double-network polymer system including a cross-linked, covalently-bonded polymer and a reversible, partially ionicly-bonded polymer, wherein the substrate has a moisture level less than or equal to 15 percent of the total weight of the substrate, and wherein the substrate includes a latent retractive force. A method for manufacturing a substrate includes producing a double-network hydrogel including a cross-linked, covalently-bonded polymer and a reversible, ionicly-bonded polymer; elongating by force the double-network hydrogel in at least one direction; dehydrating while still elongated the double-network hydrogel to form a substantially-dehydrated double-network polymer system; and releasing the force to produce the substrate.

6 Claims, No Drawings

(56) References Cited

U.S. PATENT DOCUMENTS

2015/0038613 A1    2/2015  Sun et al.

FOREIGN PATENT DOCUMENTS

| CN | 102827333 A | 12/2012 |
|---|---|---|
| EP | 2026063 A1 | 2/2009 |
| JP | 2005/526879 A | 9/2005 |
| JP | 2008542518 A | 11/2008 |
| KR | 10-2002-0073553 A | 9/2002 |
| RU | 2298022 C2 | 4/2007 |
| WO | WO 2006/132661 A1 | 12/2006 |
| WO | WO 2014/169119 A1 | 10/2014 |
| WO | WO 2014/176304 A1 | 10/2014 |
| WO | 15013306 A1 | 1/2015 |

OTHER PUBLICATIONS

Zhang, Huijuan et al., 'Thermal-responsive poly(N-isopropyl acrylamide)/sodium alginate hydrogel: preparation, swelling behaviors, and mechanical properties,' Colloid Polym Sci (2016) 294:1959-1967, published online on Oct. 12, 2016.

* cited by examiner

MATERIALS THAT SHRINK IN ONE DIMENSION AND EXPAND IN ANOTHER DIMENSION

BACKGROUND

The present disclosure is generally directed to absorbent and shrinkable materials. In particular, the present disclosure is directed to materials that shrink in one dimension and expand in another dimension when absorbing a liquid such as water or a bodily fluid.

Responsive materials that can potentially address many unmet consumer needs associated with existing products are needed. New applications of those responsive materials can also stimulate exploration and development of emerging products beyond current categories.

Related materials can include water shrinkable fibers; however, they are not hydrogels, they do not shrink to the same magnitude, and they do not possess elastic properties. Previous attempts at producing responsive materials include materials such as those described in U.S. Pat. No. 4,942,089 to Genba et al. related to shrinking fiber, water-absorbing shrinkable yarn, and other similar materials. Shrinking fibers that are hardly soluble in water and that are capable of shrinking in water at 20° C. by not less than 30% in not longer than 10 seconds are obtained, for example, by spinning, drawing, and heat-treating a carboxy-modified polyvinyl alcohol under specific conditions. Yarns made from a fiber of this kind in conjunction with nonwoven fabrics made by incorporating yarns containing such shrinking fibers in nonwoven fabrics that are shrinkable upon absorption of water have been proposed for tightly fitting edge portions of disposable diapers to the thigh.

Although capable of absorbing fluids, conventional hydrogels are generally soft and fragile in a hydrated state and brittle and hard in a dried or dehydrated state. Conventional hydrogels have poor mechanical properties with poor stretchability and notch-resistance.

In addition, U.S. Patent Application Publication Number 2015/038613 to Sun et al. describes a hydrogel composition, but does not disclose drying/dehydrating such a composition under stress. PCT Patent Application Publication Number WO06132661 to Muratoglu et al. describes a hydrogel that is made "tougher" by dehydrating the hydrogel after "deforming" the hydrogel using compressive force.

As a result, there is a need to enable production of a nonwoven with the attributes described herein.

SUMMARY

Unmet needs for existing products include conformance, comfort, and the elimination of leakage. Disclosed herein is a new type of responsive materials in different forms that can simultaneously shrink in one dimension and expand in one or more other dimensions upon contact with aqueous media and body fluids to form hydrogel materials. The materials also have significant absorbing capacity for water and other aqueous liquids. The materials are flexible.

Recently a new class of hydrogels, double-networked hydrogels, has been developed with very interesting mechanical properties such as high elasticity, toughness, and notch-resistance in hydrated state. Those materials can be used to address unmet needs in many different fields.

This disclosure describes a substrate that includes a double-network polymer system including a cross-linked, covalently-bonded polymer and a reversible, partially ionicly-bonded polymer, wherein the substrate has a moisture level less than or equal to 15 percent of the total weight of the substrate, and wherein the substrate includes a latent retractive force.

In an alternate aspect, a method for manufacturing a substrate includes producing a double-network hydrogel including a cross-linked, covalently-bonded polymer and a reversible, ionicly-bonded polymer; elongating by force the double-network hydrogel in at least one direction; dehydrating while still elongated the double-network hydrogel to form a substantially-dehydrated double-network polymer system; and releasing the force to produce the substrate.

Objects and advantages of the disclosure are set forth below in the following description, or can be learned through practice of the disclosure.

DETAILED DESCRIPTION

As used herein the term "nonwoven fabric or web" refers to a web having a structure of individual fibers or threads that are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which can be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto. Generally speaking, meltblown fibers can be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., U.S. Pat. No. 4,340,563 to Appel, et al. and U.S. Pat. No. 5,382,400 to Pike, et al., which are incorporated herein in their entirety by reference hereto thereto. Spunbond fibers are generally not tacky when they are deposited onto a collecting surface. Spunbond fibers can sometimes have diameters less than about 40 microns, and are often between about 5 to about 20 microns.

As used herein the term "staple fiber" means fibers that have a fiber length generally in the range of about 0.5 to about 150 millimeters. Staple fibers can be cellulosic fibers or non-cellulosic fibers. Some examples of suitable non-cellulosic fibers that can be used include, but are not limited to, hydrophilically-treated polyolefin fibers, polyester fibers, nylon fibers, polyvinyl acetate fibers, and mixtures thereof. Hydrophilic treatments can include durable surface treatments and treatments in polymer resins/blends. Cellulosic staple fibers include for example, pulp, thermomechanical pulp, synthetic cellulosic fibers, modified cellulosic fibers, and the like. Cellulosic fibers can be obtained from secondary or recycled sources. Some examples of suitable cellulosic fiber sources include virgin wood fibers, such as thermomechanical, bleached and unbleached softwood and hardwood pulps. Secondary or recycled cellulosic fibers can be obtained from office waste, newsprint, brown paper stock, and paperboard scrap. Further, vegetable fibers, such as abaca, flax, milkweed, cotton, modified cotton, cotton linters, can also be used as the cellulosic fibers. In addition, synthetic cellulosic fibers such as, for example, rayon, viscose rayon and lyocell can be used. Modified cellulosic fibers are generally composed of derivatives of cellulose formed by substitution of appropriate radicals (e.g., carboxyl, alkyl, acetate, nitrate, etc.) for hydroxyl groups along the carbon chain. Desirable staple fibers for the purposes of this application are hydrophilic, such as traditional cellulosic fibers (a desirable example of which is pulp fibers, as can be found in rolled tissues and paper-based towels).

As used herein, the term "substantially continuous fibers" is intended to mean fibers that have a length that is greater than the length of staple fibers. The term is intended to include fibers that are continuous, such as spunbond fibers, and fibers that are not continuous, but have a defined length greater than about 150 millimeters.

As used herein "bonded carded webs" or "BCW" refers to nonwoven webs formed by carding processes as are known to those skilled in the art and further described, for example, in U.S. Pat. No. 4,488,928 to Ali Khan et al., which is incorporated herein by reference thereto. Briefly, carding processes involve starting with a blend of, for example, staple fibers with bonding fibers or other bonding components in a bulky ball that is combed or otherwise treated to provide a generally uniform basis weight. This web is heated or otherwise treated to activate the adhesive component resulting in an integrated, usually lofty nonwoven material.

The basis weight of nonwoven webs is usually expressed in ounces of material per square yard (osy) or grams per square meter (gsm) and fiber diameters are usually expressed in microns, or in the case of staple fibers, denier. It is noted that to convert from osy to gsm, multiply osy by 33.91.

As used herein the terms "machine direction" or "MD" generally refers to the direction in which a material is produced. It is also often the direction of travel of the forming surface onto which fibers are deposited during formation of a non-woven web. The term "cross-machine direction" or "CD" refers to the direction perpendicular to the machine direction. Dimensions measured in the cross-machine direction (CD) are referred to as "width" dimensions, while dimensions measured in the machine direction (MD) are referred to as "length" dimensions. The width and length dimensions of a planar sheet make up the X and Y directions of the sheet. The dimension in the depth direction of a planar sheet is also referred to as the Z-direction.

As used herein, the terms "elastomeric" and "elastic" are used interchangeably and shall mean a layer, material, laminate or composite that is generally capable of recovering its shape after deformation when the deforming force is removed. Specifically, when used herein, "elastic" or "elastomeric" is meant to be that property of any material that, upon application of a biasing force, permits the material to be stretchable to a stretched biased length that is at least about fifty (50) percent greater than its relaxed unbiased length, and that will cause the material to recover at least forty (40) percent of its elongation upon release of the stretching force. A hypothetical example that would satisfy this definition of an elastomeric material would be a one (1) inch sample of a material that is elongatable to at least 1.50 inches and that, upon being elongated to 1.50 inches and released, will recover to a length of less than 1.30 inches. Many elastic materials can be stretched by much more than fifty (50) percent of their relaxed length, and many of these will recover to substantially their original relaxed length upon release of the stretching force.

As used herein, the term "g/cc" generally refers to grams per cubic centimeter.

As used herein, the term "hydrophilic" generally refers to fibers or films, or the surfaces of fibers or films that are wettable by aqueous liquids in contact with the fibers. The term "hydrophobic" includes those materials that are not hydrophilic as defined. The phrase "naturally hydrophobic" refers to those materials that are hydrophobic in their chemical composition state without additives or treatments affecting the hydrophobicity.

The degree of wetting of the materials can, in turn, be described in terms of the contact angles and the surface tensions of the liquids and materials involved. Equipment and techniques suitable for measuring the wettability of particular fiber materials or blends of fiber materials can be provided by the Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

Reference now will be made in detail to various aspects of the disclosure, one or more examples of which are set forth below. Each example is provided by way of explanation, not of limitation of the disclosure. In fact, it will be apparent to those skilled in the art that various modifications and variations can be made in the present disclosure without departing from the scope or spirit of the disclosure. For instance, features illustrated or described as part of one aspect, can be used on another aspect to yield a still further aspect. Thus it is intended that the present disclosure cover such modifications and variations.

This disclosure describes a modification of a double-network hydrogel. A double-network hydrogel is a hydrogel that includes two types of polymers. In this case, one is a cross-linked/covalently-bonded polymer; the second is a reversible/ionicly-bonded polymer. Double-network hydrogels have been reported to have superior mechanical properties such as strength, elasticity, and notch-resistance. (See, e.g., Nature, Vol. 489, p 133, 2012).

The double-network hydrogel of this disclosure is modified by stretching/stressing the double-network hydrogel while it is wet and then, while maintaining such stretching, drying it to lower than about a 10-15% moisture level. The resultant product material, a double-network polymer system that is not a hydrogel, remains strong and flexible when dry, but is not elastic. The cross-linked polymer of the double-network polymer system provides strength, whereas the ionicly-bonded polymer has had some of its bonds broken. Without being limited with respect to theory, it is believed that breaking these bonds during drying creates stored energy in the form of a latent retractive force in the dry double-network polymer system.

In a typical hydrogel, re-hydration leads to expansion in all three dimensions. Again, without being limited with respect to theory, it is believed that when the dry double-network polymer system of this disclosure is re-hydrated, some of the broken ionic bonds are re-formed. The double-network polymer system shrinks in one dimension (e.g., in the x-y plane), while it expands in another dimension (e.g., the z-direction, where the z-direction is perpendicular to the x-y plane). For example, a string-like sample of dry double-network polymer system demonstrated shrinkage in length from about 5 inches to 1 inch when re-hydrated, while the sample also expanded in diameter. A disk-shaped sample of the dry double-network polymer system shrank in diameter but increased in thickness.

This double-network polymer system can absorb many times its weight in water. Examples are detailed below in this disclosure.

For the purposes of this disclosure, samples of double-network hydrogels were made using polyacrylamide as the cross-linked polymer and calcium alginate as the ionicly-bonded polymer. Additional detail with respect to the preparation and performance of such double-network hydrogels can be found in U.S. Patent Application Publication Number 2015/038613 to Sun et al., which is incorporated herein by reference to the extent it does not conflict herewith.

Potential applications of the double-network polymer system include embedding the dry double-network polymer systems in personal care products, absorbent medical products, and wipers in various string lengths or shapes. The dry double-network polymer system in a product will change shape or tighten when wetted, potentially leading to a change in shape or appearance of such products.

In various aspects of the disclosure, a string/strand, or a sheet, or a fiber in a dry state (with less than or equal to 10-15% water content) shrinks in at least one dimension and expands in at least one other dimension upon contact with aqueous media. In addition, the strings/strands, sheets, or fibers absorb at least four times their weight in water. For instance, in the case of a string made from the double-network polymer system, the string's length becomes much shorter when wetted than it was in the original dry state when no external force is applied, whereas the diameter of the string becomes larger at the same time upon wetting. In another example, a sheet made from the double-network polymer system can shrink in length and width upon wetting or hydrating while its thickness increases at the same time.

In one specific aspect of the present disclosure, a material is made from at least one cross-linked hydrogel-forming polymer and at least a second hydrogel-forming polymer with reversible cross-linkers in which a significant portion of the cross-linkers (e.g., 30%) are not fully cross-linked and are in a free or partially-free state with the polymer in a dry state.

The cross-linked polymer can be polyacrylamide, polyacrylic acid, any other suitable polymer, or any combination of these. The reversible cross-linker can be alginate with calcium ions, gelatin with aluminum ions, any other suitable polymer, or any combination of these. In a dry state, calcium ions are not significantly cross-linked with alginate.

As described further in the examples below, the present disclosure includes manufacturing the double-networked polymer system substrates. First, the double-networked hydrogels are manufactured in a hydrated state consistent with reported literature. The double-network hydrogels can be manufactured in a string, a sheet, or in any other suitable form. After curing the double-network hydrogels, the double-network hydrogels are stretched or elongated in one or two selected dimensions mechanically and dried while elongated. When the elongation force is released, the dried materials (double-network polymer systems) keep the dimensions they acquired under elongation without significant changes for a long period of time under ambient conditions.

While not shown, it can be desirable to use finishing steps and/or post treatment processes to impart selected properties to the dry double-network polymer system. For example, chemical post treatments can be added to the double-network polymer system at a later step, or the double-network polymer system can be transported to cutters, slitters, or other processing equipment for converting the double-network polymer system into a final product. Further, patterning can be placed through known processes into the outer surfaces of the double-network polymer system.

EXAMPLES

Materials and Procedures

1. Preparation of Double Network Hydrogel.

In one vial, 1.7 g of acrylamide and 0.3 g of alginate sodium were dissolved in 12 ml of water. Then 1 mg of N,N'-Methylenebisacrylamide (MBAA) and 17 mg of ammonium persulfate were added. In a second vial, 4.2 mg of tetramethyl ethylenediamine was dissolved in 1 ml of water and 40 mg of calcium sulfate were mixed. The two solutions were degassed under vacuum for half an hour. The two solutions were then mixed and poured into a petri dish. The petri was covered with a piece of glass and was placed under a hand-held UV lamp for two hours to form and cure the hydrogel. The hydrogel is elastic and can be easily stretched to 20 times its original length without breaking. The stretch and relaxation can be repeated more than 20 times.

2. Preparation of Water-Triggered Shrinkable Strings.

The hydrogel piece prepared in preparation step 1 was cut into small strings. The strings were stretched to about 6 times their original lengths and were air-dried. Each air-dried string remained stable and was flexible for bending and manipulation without breaking. The air-dried strings shrank to lengths close to their lengths in their original hydrated states within a couple of minutes upon wetting with water or urine. For example, a thin shrinkable string with a length of 12 cm became a relatively fat hydrogel string with a length of 2 cm. In comparison, polyvinyl alcohol-based shrinkable fibers of similar size shrank less than 50% and shrank more slowly.

3. Preparation of Water-Triggered Shrinkable Disk.

The hydrogel piece prepared in preparation step 1 was cut into small disks. The disks were stretched to about 4 times their original diameters and were air-dried. Each air-dried disk remained stable and was flexible for bending and manipulation without breaking. The dry disks shrank into diameters close to their diameters in their original hydrated states within a couple of seconds upon wetting with water or urine. For example, a thin, shrinkable disk with a length of 2 cm became a relatively thick hydrogel disk with a diameter of 0.5 cm within 5 seconds after wetting.

Results

4. Water Absorption.

A shrinkable string with a weight of 5 mg was prepared as described in preparation step 2, and then soaked with water for 5 minutes. A bundle of polyvinyl alcohol-based shrinkable fiber with a total weight of 5 mg was soaked with water for 5 minutes. The hydrated materials were laid on a piece of paper towel to absorb most of free water by slightly squeezing the materials against the paper towel for a few seconds, and then weighed. The shrinkable string absorbed 23 mg of water while the bundle shrinkable fiber absorbed 6 mg of water.

5. Tissue Embedded with the Shrinkable Strings.

Dried strings were prepared as described in preparation step 2. Two dried strings were embedded in parallel in one piece of tissue using adhesive. Another two dried strings were embedded diagonally in another piece of tissue using adhesive. Another dried string was embedded in a circular shape in a third piece of tissue using adhesive. Wetting each sample with water resulted in the shrinkable strings shrinking in length and pulling the tissue samples into different three dimensional structures depending on the orientation of the shrinkable strings on each tissue.

6. Nonwoven Materials with the Shrinkable Strings.

One piece of nonwoven material was prepared. Two dried strings prepared as in preparation step 2 were embedded on the nonwoven material in parallel using adhesive. A second piece of nonwoven material was prepared. Two dried strings prepared as in preparation step 2 were embedded on the nonwoven material diagonally using adhesive. Wetting each sample with water resulted in the shrinkable strings shrinking in length and pulling the nonwoven material samples into different three dimensional structures depending on the orientation of the shrinkable strings in each sample.

In a first particular aspect, a substrate includes a double-network polymer system including a cross-linked, covalently-bonded polymer and a reversible, partially ionicly-bonded polymer, wherein the substrate has a moisture level less than or equal to 15 percent of the total weight of the substrate, and wherein the substrate includes a latent retractive force.

A second particular aspect includes the first particular aspect, wherein the substrate is liquid absorbent.

A third particular aspect includes the first and/or second aspect, wherein the cross-linked, covalently-bonded polymer is polyacrylamide.

A fourth particular aspect includes one or more of aspects 1-3, wherein the reversible, partially ionicly-bonded polymer is calcium alginate.

A fifth particular aspect includes one or more of aspects 1-4, wherein the substrate is flexible and inelastic.

A sixth particular aspect includes one or more of aspects 1-5, wherein the substrate is configured to release the retractive force when exposed to aqueous liquid.

A seventh particular aspect includes one or more of aspects 1-6, wherein the release of the retractive force results in the substrate shrinking in at least one dimension.

An eighth particular aspect includes one or more of aspects 1-7, wherein the release of the retractive force results in the substrate expanding in at least one dimension that is different from the shrinking dimension.

A ninth particular aspect includes one or more of aspects 1-8, wherein the double-network polymer system is configured to become a double-network hydrogel when exposed to aqueous liquid.

In a tenth particular aspect, a method for manufacturing a substrate includes producing a double-network hydrogel including a cross-linked, covalently-bonded polymer and a reversible, ionicly-bonded polymer; elongating by force the double-network hydrogel in at least one direction; dehydrating while still elongated the double-network hydrogel to form a substantially-dehydrated double-network polymer system; and releasing the force to produce the substrate.

An eleventh particular aspect includes the tenth particular aspect, wherein dehydrating dries the double-network polymer system to less than or equal to 15% moisture of the total weight of the double-network polymer system.

A twelfth particular aspect includes tenth and/or eleventh particular aspects, wherein elongating and dehydrating captures a latent retractive force in the substrate.

A thirteenth particular aspect includes one or more of aspects 10-12, wherein the substrate is configured to release the retractive force when exposed to liquid.

A fourteenth particular aspect includes one or more of aspects 10-13, wherein the release of the retractive force results in the substrate shrinking in at least one dimension.

A fifteenth particular aspect includes one or more of aspects 10-14, wherein the release of the retractive force results in the substrate expanding in at least one dimension that is different from the shrinking dimension.

A sixteenth particular aspect includes one or more of aspects 10-15, wherein the cross-linked, covalently-bonded polymer is polyacrylamide.

A seventeenth particular aspect includes one or more of aspects 10-16, wherein the reversible, ionicly-bonded polymer is calcium alginate.

An eighteenth particular aspect includes one or more of aspects 10-17, wherein the double-network hydrogel is elastic, and wherein the substrate is flexible and inelastic.

A nineteenth particular aspect includes one or more of aspects 10-18, wherein the double-network polymer system is configured to return to a double-network hydrogel when exposed to aqueous liquid.

A twentieth particular aspect includes one or more of aspects 10-19, wherein the substrate is in the form of a web, a string, a disk, a sheet, or a fiber.

While the disclosure has been described in detail with respect to the specific aspects thereof, it will be appreciated that those skilled in the art, upon attaining an understanding of the foregoing, can readily conceive of alterations to, variations of, and equivalents to these aspects. Accordingly, the scope of the present disclosure should be assessed as that of the appended claims and any equivalents thereto.

What is claimed is:

1. A substrate comprising:
a double-network polymer system including a cross-linked, covalently-bonded polymer and a reversible, partially ionicly-bonded polymer, wherein the substrate has a moisture level less than or equal to 15 percent of the total weight of the substrate, wherein the substrate comprises a latent retractive force and is configured to release the retractive force when exposed to aqueous liquid, wherein the release of the retractive force results in the substrate shrinking in at least one dimension, and wherein the release of the retractive force results in the substrate expanding in at least one dimension that is different from the at least one dimension in which the substrate shrinks.

2. The substrate of claim 1, wherein the substrate is liquid absorbent.

3. The substrate of claim 1, wherein the cross-linked, covalently-bonded polymer is polyacrylamide.

4. The substrate of claim 1, wherein the reversible, partially ionicly-bonded polymer is calcium alginate.

5. The substrate of claim 1, wherein the substrate is flexible and inelastic.

6. The substrate of claim 1, wherein the double-network polymer system is configured to become a double-network hydrogel when exposed to aqueous liquid.

* * * * *